US00PP35562P2

(12) United States Plant Patent
Van Swieten

(10) Patent No.: US PP35,562 P2
(45) Date of Patent: Dec. 26, 2023

(54) ***PHALAENOPSIS* ORCHID PLANT NAMED 'PHA932414'**

(50) Latin Name: ***Phalaenopsis* hybrid**
Varietal Denomination: PHA932414

(71) Applicant: ANTHURA B.V., Bleiswijk (NL)

(72) Inventor: Martinus Nicolaas Gerardus Van Swieten, Utrecht (NL)

(73) Assignee: Anthura, B.V., Bleiswijk (NL)

( * ) Notice: Subject to any disclaimer, the term of this patent is extended or adjusted under 35 U.S.C. 154(b) by 0 days.

(21) Appl. No.: 18/445,170

(22) Filed: May 4, 2023

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP33,098 P2 * 5/2021 Van Swieten ..... Plt./311

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHA932414', particularly characterized by numerous small, very light purple, striped flowers with small white edges, reddish-purple lips, and is propagated by meristem tissue culture, is disclosed.

3 Drawing Sheets

Genus and species: *Phalaenopsis* hybrid.
Variety denomination: 'PHA932414'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA932414'.

The new *Phalaenopsis* plant is a product of a planned breeding program conducted by the inventor in Bleiswijk, the Netherlands. The objective of this breeding program was to create a new *Phalaenopsis* plant having numerous small, very light purple, striped flowers with small white edges and reddish-purple lips, suitable for potted plant production.

The new *Phalaenopsis* plant 'PHA932414' is a result of cross-pollination made by the inventor in April 2013 in Bleiswijk, the Netherlands, of the proprietary female, or seed parent, *Phalaenopsis* hybrid '00001-3358' (unpatented) with the proprietary male, or pollen parent, *Phalaenopsis* hybrid '00001-4627' (unpatented).

The new *Phalaenopsis* was selected by the inventor as a single plant within the progeny of the stated cross-pollination in a controlled greenhouse in Bleiswijk, the Netherlands, in March 2017. Asexual reproduction of the new *Phalaenopsis* plant by meristem tissue culture since 2018 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Aug. 24, 2022 (Application no. 2022/1977), by Applicant who obtained the subject matter disclosed directly from the inventor. 'PHA932414' has not been made publicly available or sold anywhere in the world prior to the effective filing date of this application with the exception of sales or disclosures made one year or less before the effective filing date of this claimed invention by Applicant who obtained PHA932414' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA932414' as a new and distinct variety of *Phalaenopsis* plant:

1) Small, very light purple, striped flowers with small white edges and reddish-purple lips;
2) Lips have short whiskers; and
3) Plant has many branches.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in February 2023. Colors in the photographs may differ from the color values cited in the detailed botanical description, which accurately describe the actual colors of the new variety.

DESCRIPTION OF THE NEW VARIETY

Figure 1:
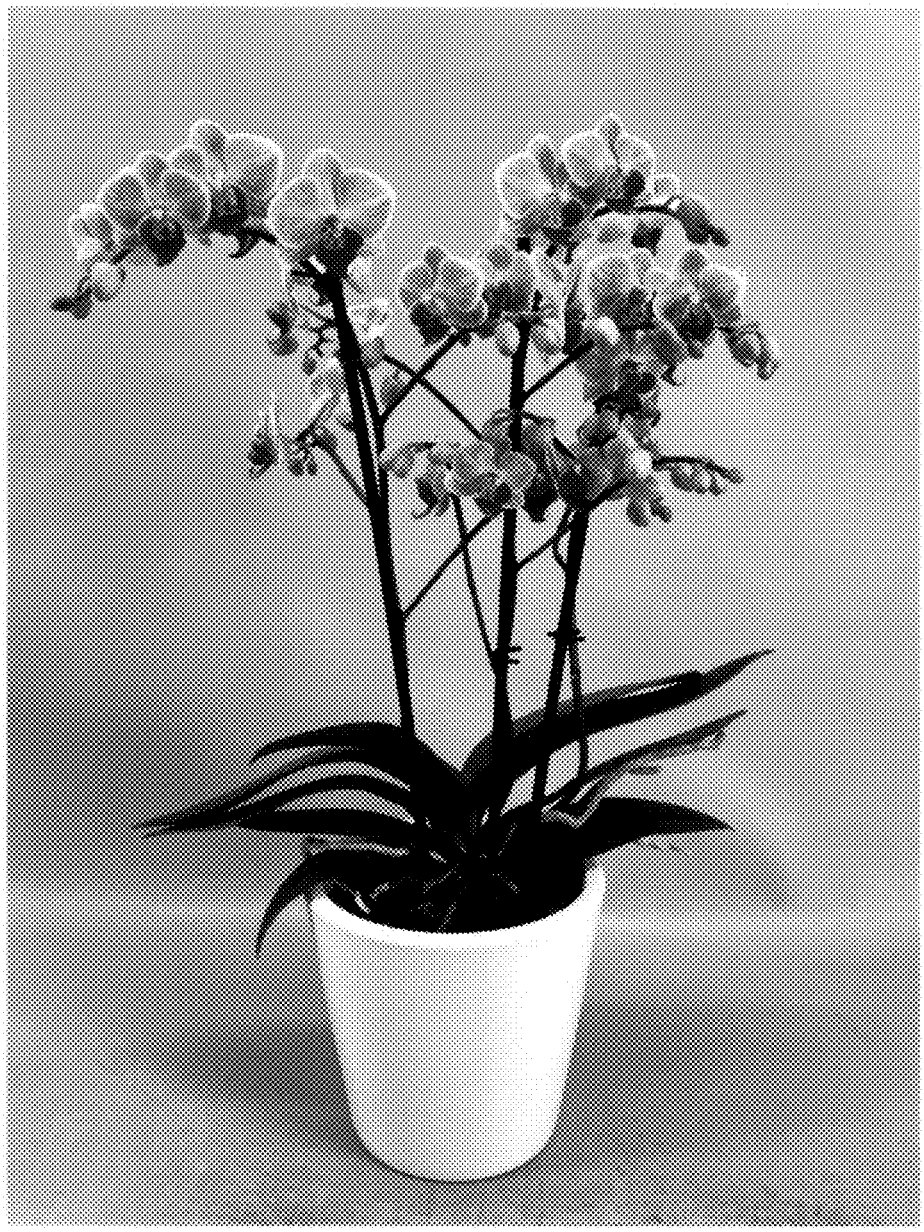
FIG. 1 shows the overall plant habit, including blooms, buds, and foliage, of 'PHA932414'.
Figure 2:
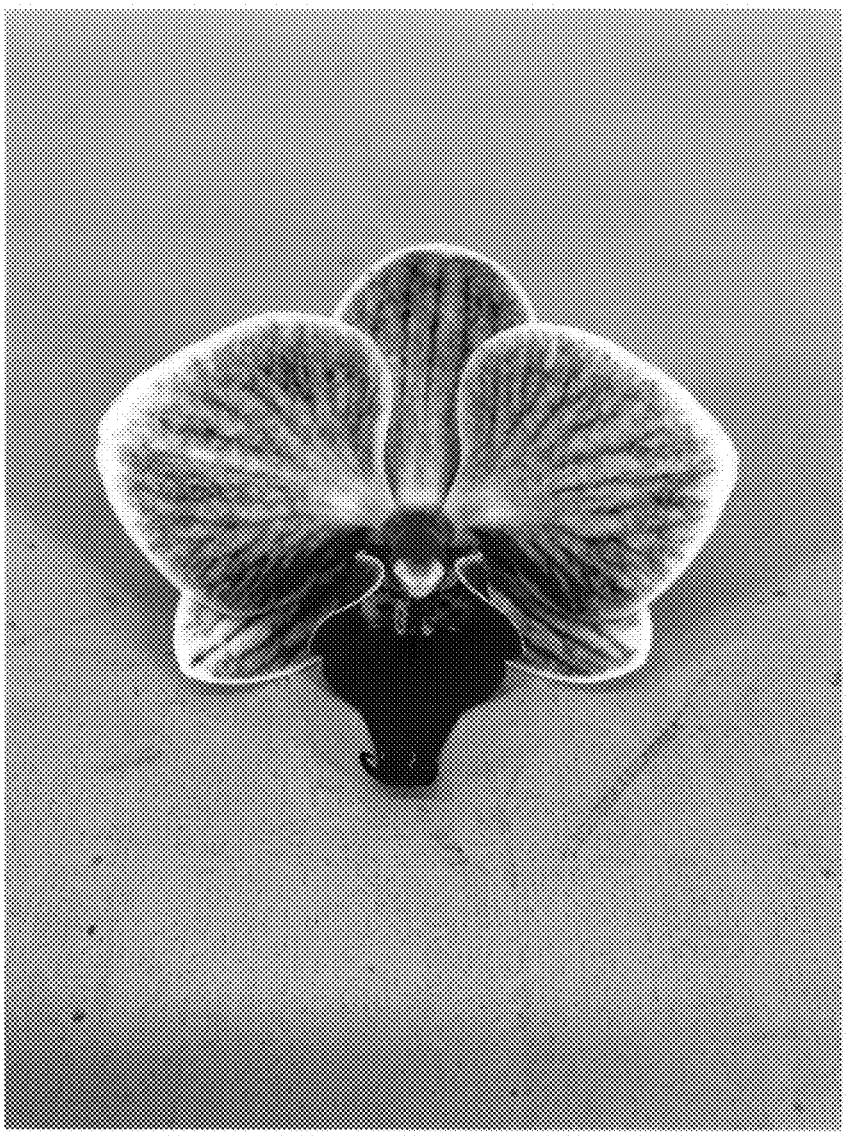
FIG. 2 shows a close-up of a flower of 'PHA932414'.
Figure 3:
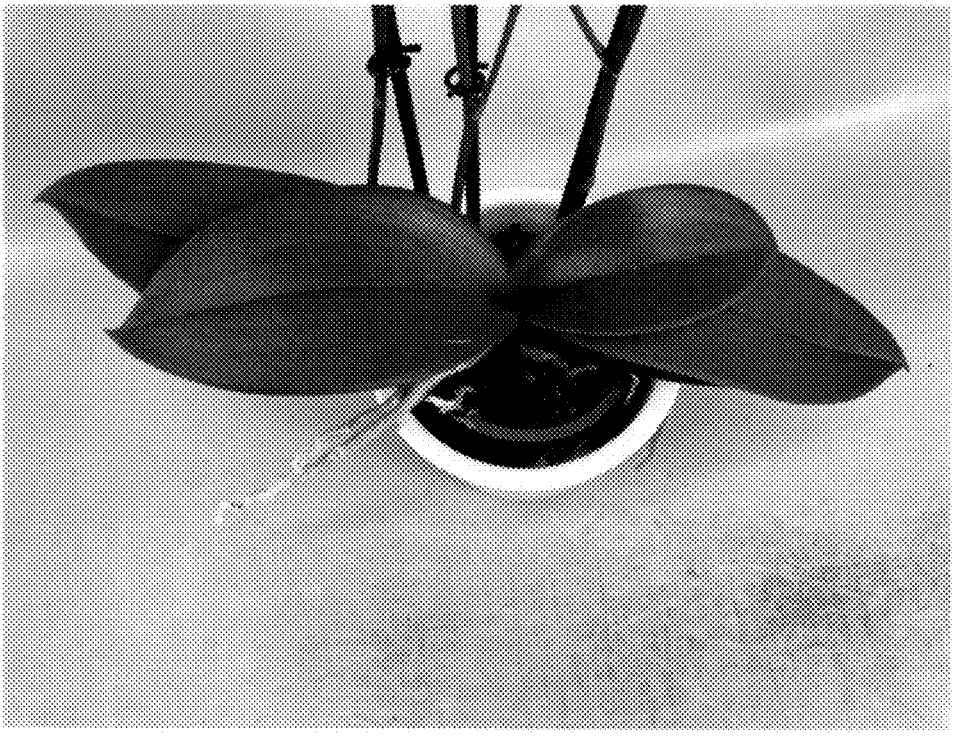
FIG. 3 shows an overhead, close-up view of the leaves of 'PHA932414'.

The following detailed description sets forth the distinctive characteristics of 'PHA932414'. Plants of the new *Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in February 2023 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:
- *Family*.—Orchidaceae.
- *Botanical*.—*Phalaenopsis* hybrid.
- *Common name*.—Moth orchid.
- *Variety name*.—'PHA932414'.

Parentage:
- *Female parent*.—*Phalaenopsis* cultivar '00001-3358' (unpatented).
- *Male parent*.—*Phalaenopsis* cultivar '00001-4627' (unpatented).

Propagation:
- *Type*.—Meristem tissue culture.

Roots:
- *Root description*.—Greyed-green (a color between RHS 190B and 190C) colored roots with branching lateral roots having yellow-green colored root tips (RHS 144C).

Plant:
- *Commercial crop time to flowering*.—Following asexual propagation (in vitro), the rooted cuttings grow for 20-24 weeks. After transplantation into 12-cm pots, the plants are finished after 48 to 50 weeks.
- *Growth habit of the peduncle*.—Upright to slightly pendent with panicle inflorescence.
- *Height (from soil level to top of inflorescence)*.—Approximately 35.0 cm to 40.0 cm.
- *Width (measured from leaf tips)*.—About 33.0 cm to 35.0 cm.
- *Vigor*.—Strong.

Leaves:
- *Mature leaves*.—Quantity per plant: 10 to 12 leaves are produced before flowering. Length (fully expanded): 17.0 cm to 19.0 cm. Width: 6.5 cm to 7.5 cm. Position of the broadest part of the leaf: At the middle. Shape: Oblong. Base shape: Moderately elongated. Apex: Acute asymmetric. Leaf blade angle with the petiole (measured from the horizontal position): Between 5 degrees and 20 degrees. Leaf margin: Entire. Color: Upper surface: RHS 147A. Lower surface: RHS 147B. Texture (both upper and lower surfaces): Smooth. Thickness: 1.0 mm to 2.0 mm. Variegation: Absent. Venation: Pattern: Parallel. Color of the midvein: Upper surface: RHS 147A. Lower surface: RHS 147B.

Peduncle:
- *Quantity per plant*.—3.
- *Number of flowers per peduncle*.—20 to 30.
- *Length*.—35.0 cm to 40.0 cm.
- *Diameter*.—4.0 mm to 5.0 mm.
- *Strength*.—Strong.
- *Aspect*.—Upright to slightly pendent.
- *Texture*.—Smooth.
- *Color*.—Green (RHS 146A).
- *Internode length*.—1.0 cm to 2.0 cm.

Inflorescence description:
- *Appearance*.—Upright to slightly pendent, panicle inflorescence with bilaterally symmetrical flowers that open in succession beginning with the lowermost flower.
- *Number of inflorescences*.—3.
- *Inflorescence size*.—Height (from base to tip): 200.0 mm to 270.0 mm.
- *Flowering time*.—First flowers can be expected 10 to 11 months after planting in a 12-cm pot.
- *Flower*.—Height: 45.0 mm to 50.0 mm. Diameter: 53.0 mm to 58.0 mm. Depth of lip: 17.0 mm to 19.0 mm.
- *Flower longevity*.—On the plant: 9 to 11 weeks.
- *Flower shape in lateral view*.—Flat.
- *Fragrance*.—Absent.
- *Flower bud*.—Average size: Medium. Length: 16.0 mm to 18.0 mm. Width: 14.0 mm to 16.0 mm. Shape: Egg shaped. Color: Light yellow-green (RHS 145B) with a touch of purplish-pink (RHS N78C) toward the tip.
- *Petals*.—Arrangement: Open/free. Shape: Semi-circular. Apex: Obtuse asymmetric. Margin: Entire. Length (from base to tip): 25.0 mm to 27.0 mm. Width: 28.0 mm to 30.0 mm. Position of the broadest part of the petal: Toward the base. Color (when fully opened): Upper surface: Basic color: Very light purple (RHS 76B). Over color: Reddish-purple stripes and netting (RHS N78B); white edge (RHS NN155C). Lower surface: Basic color: Very light purple (RHS 76C). Over color: Light reddish-purple shade (RHS N78D) toward the margin and white margin (RHS NN155C). Number of spots and stripes on the petals (upper surface): Many stripes. Color of spots and stripes on the petals (upper surface): RHS N78B. Density of netting of the petals (upper surface): Medium. Color of the netting (upper surface): RHS N78B.
- *Dorsal sepal*.—Shape: Elliptic. Apex: Rounded symmetric. Margin: Entire. Length (from base to tip): 25.0 mm to 27.0 mm. Width: 18.0 mm to 20.0 mm. Position of the broadest part of the dorsal sepals: At the middle. Color (when fully opened): Upper surface: Basic color: Light purple (RHS 76A). Over color: Reddish-purple stripes and netting (RHS N78B); white edge (RHS NN155C). Lower surface: Basic color: Light purple (RHS 76B). Over color: Light purple shade (RHS 76A) toward edge; white edge (RHS NN155C). Number of spots and stripes on the dorsal sepals (upper surface): Medium stripes. Color of spots and stripes on the dorsal sepals (upper surface): RHS N78B. Density of netting of the dorsal sepals (upper surface): Low. Color of the netting (upper surface): RHS N78B.

*Lateral sepals*.—Shape: Ovate. Apex: Obtuse asymmetric. Margin: Entire. Length (from base to tip): 26.0 mm to 28.0 mm. Width: 17.0 mm to 19.0 mm. Position of the broadest part of the lateral sepals: Toward the base. Color (when fully opened): Upper surface: Basic color: Very light purple (RHS 76B). Over color: Touch of light yellow-green (RHS 145D) and very small purplish-red spots (RHS 64A) at the base; reddish-purple stripes and netting (RHS N78B). Lower surface: Basic color: Very light purple (RHS 76C). Over color: Light yellow-green (RHS 145C) and light reddish-purple (RHS N78D) toward margins; white edge (RHS NN155C). Number of spots and stripes on the lateral sepals (upper surface): Medium spots and medium stripes. Color of spots and stripes on the lateral sepals (upper surface): Spots RHS 64A; stripes RHS N78B. Density of netting of the lateral sepals (upper surface): Low. Color of the netting (upper surface): RHS N78B.

*Labellum* (*lip*).—Whiskers: Present. Length of whiskers: 7.0 mm to 9.0 mm. Color of whiskers: Reddish-purple (RHS N78A) with small white tips (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Moderately undulated. Length: 14.0 mm to 16.0 mm. Width: 10.0 mm to 12.0 mm. Color: Upper surface: White (RHS 155C) at the base with a touch of light greenish-yellow (RHS 8B); red stripes (RHS 183C) at the base towards one margin; purplish-red margin (RHS 71A) on one side; reddish-purple (RHS N78B) toward the tip. Lower surface: Greenish-white (RHS 155C) at the base toward margin on one side; purplish-red (RHS 71A) at the base toward margin on the other side; reddish-purple (RHS N78B) toward tip. Number of spots and stripes on the lateral lobe: Few stripes. Color of spots and stripes on the lateral lobe: RHS 183C. Density of netting of the lateral lobe: None. Color of the netting: None.

*Apical lobe*.—Shape: Triangular. Margin: Entire. Length: 17.0 mm to 19.0 mm. Width: 18.0 mm to 20.0 mm. Color: Upper surface: Red margin (RHS 183C) and a touch of yellow (RHS 8A) at the base; purplish-red (RHS 59B) toward wings; reddish-purple (RHS N78A) toward whiskers. Lower surface: Dark red margin (RHS 183B) at the base toward wings; greenish-white (RHS 155C) at the middle from the base; reddish-purple (RHS N78A) toward edge on both sides and whiskers. Number of spots and stripes on the apical lobe: None. Color of spots and stripes on the apical lobe: Not applicable. Density of netting of the apical lobe: None. Color of the netting: Not applicable. Bump and ridge: Absent.

*Callus*.—Average size: Small. Height: 4.0 mm to 5.0 mm. Length: 4.0 mm to 5.0 mm. Width: 3.0 mm to 4.0 mm. Color: Greenish-yellow (RHS 5B) toward tips; yellow-white (RHS 155B) on sides; dotted RHS 183C.

Reproductive organs:

*Column*.—Length: 7.0 mm to 8.0 mm. Diameter: 4.0 mm to 5.0 mm. Color: Reddish-purple (RHS N78B).

*Pollinia*.—Quantity: 2. Diameter: 0.7 mm to 0.9 mm. Color: Orange (RHS 24A).

*Ovary*.—Length: 8.0 mm to 10.0 mm. Diameter: 1.6 mm to 1.8 mm.

*Pedicel*.—Length: 32.0 mm to 34.0 mm. Diameter: 1.9 mm to 2.1 mm. Texture: Smooth. Color: Light yellow-green (RHS 145B) at the base; lighter yellow-green (RHS 145D) with a touch of purplish-red (RHS N77B) at the base and toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA932414' differs from the female parent plant '00001-3358' (unpatented), in that 'PHA932414' has a greenish-yellow callus, concave dorsal sepal in cross section, and very light purple petals on upper surface, whereas '00001-3358' has a very light yellow callus, straight dorsal sepal in cross section, and purplish-pink petals on upper surface.

'PHA932414' differs from the male parent plant '00001-4627' (unpatented) in that 'PHA932414' has a greenish-yellow callus and upper surface of petals is very light purple with no flecks, whereas '00001-4627' has a dark red callus and upper surface of petals is white with a medium number of flecks.

'PHA932414' is most similar to the commercial *Phalaenopsis* plants named 'PHALGYMA' (U.S. Plant Pat. No. 33,098) and 'PHALDONFI' (U.S. Plant Pat. No. 26,066). 'PHA932414' differs from the commercial variety 'PHALGYMA' in that 'PHA932414' has longer, moderately elongated leaves, green peduncles, and short whiskers, whereas 'PHALGYMA' has shorter, slightly elongated leaves, a mix of brown and green peduncles, and very short whiskers.

'PHA932414' differs from the commercial variety 'PHALDONFI' in that 'PHA932414' has flat petals in cross section, green peduncles, and a shorter internode, whereas 'PHALDONFI' has concave petals in the cross section, brown peduncles, and a longer internode. Additionally, 'PHA932414' has short whiskers, whereas 'PHALDONFI' does not have whiskers.

I claim:

1. A new and distinct variety of *Phalaenopsis* plant named 'PHA932414', substantially as described and illustrated herein.

* * * * *